United States Patent
Habib

(10) Patent No.: US 9,011,430 B2
(45) Date of Patent: Apr. 21, 2015

(54) LUMENAL REMODELING DEVICE AND METHODS

(75) Inventor: Nagy Habib, Hitchin (GB)

(73) Assignee: Emcision Limited, London (GB)

( * ) Notice: Subject to any disclaimer, the term of this patent is extended or adjusted under 35 U.S.C. 154(b) by 363 days.

(21) Appl. No.: 13/503,598

(22) PCT Filed: Nov. 4, 2010

(86) PCT No.: PCT/GB2010/051845
§ 371 (c)(1),
(2), (4) Date: Apr. 25, 2012

(87) PCT Pub. No.: WO2011/055143
PCT Pub. Date: May 12, 2011

(65) Prior Publication Data
US 2012/0232326 A1    Sep. 13, 2012

(30) Foreign Application Priority Data

Nov. 4, 2009 (GB) .................................... 0919336.8
Jun. 24, 2010 (GB) .................................... 1010641.7

(51) Int. Cl.
*A61B 18/18* (2006.01)
*A61B 18/04* (2006.01)
(Continued)

(52) U.S. Cl.
CPC ............. *A61B 17/22* (2013.01); *A61B 17/2202* (2013.01); *A61B 18/082* (2013.01); *A61B 18/14* (2013.01);
(Continued)

(58) Field of Classification Search
CPC ............... A61B 17/2202; A61B 18/14; A61B 18/1492; A61B 18/1815; A61B 18/08; A61B 2017/00243; A61B 2018/00577; A61B 2018/00214; A61B 2018/00351; A61B 2218/002

USPC .......................................... 606/41, 33, 27–32
See application file for complete search history.

(56) References Cited

U.S. PATENT DOCUMENTS 6,411,852 B1 *   6/2002   Danek et al. ................... 607/42
7,291,146 B2 *   11/2007  Steinke et al. .................. 606/41
(Continued)

FOREIGN PATENT DOCUMENTS

CN    1223180    7/1999
CN    1278711    10/2006
(Continued)

OTHER PUBLICATIONS

First Office Action dated Apr. 30, 2014, issued in Chinese Patent Application 201080050067.6.

*Primary Examiner* — Catherine Voorhees
(74) *Attorney, Agent, or Firm* — Baker & Hostetler LLP

(57) ABSTRACT

A device and method suitable for remodelling the internal surface of a hollow vessel at least partially occluded by a mass is provided. The device comprises an elongate body having a distal end and a proximal end, the distal end comprising a tip portion located at the distal terminus of the body, and at least one heating element located proximally to the tip portion within the distal end. The at least one heating element is configured to be greater in dimension proximally than distally and thereby tapers towards the distal end. Furthermore, the at least one heating element is arranged so that it can be deployed outwardly from the body of the device and in so doing exert an expansion force on the hollow vessel. The at least one heating element is capable of delivering sufficient energy to remodel the internal surface, and if necessary caused localized ablation, of the hollow vessel without inducing closure of the hollow vessel.

20 Claims, 13 Drawing Sheets

(51) Int. Cl.
*A61B 17/22* (2006.01)
*A61B 18/14* (2006.01)
*A61B 18/08* (2006.01)
*A61B 18/24* (2006.01)
*A61B 19/00* (2006.01)
*A61B 17/00* (2006.01)
*A61B 18/00* (2006.01)
*A61B 18/12* (2006.01)
*A61F 2/01* (2006.01)

(52) U.S. Cl.
CPC ......... *A61B 18/1492* (2013.01); *A61B 18/1815* (2013.01); *A61B 18/245* (2013.01); *A61B 19/46* (2013.01); *A61B 2017/00022* (2013.01); *A61B 2017/00867* (2013.01); *A61B 2017/22038* (2013.01); *A61B 2017/22061* (2013.01); *A61B 2017/22079* (2013.01); *A61B 2018/00214* (2013.01); *A61B 2018/0022* (2013.01); *A61B 2018/00821* (2013.01); *A61B 2018/00898* (2013.01); *A61B 2018/126* (2013.01); *A61B 2018/1861* (2013.01); *A61B 2019/5278* (2013.01); *A61B 2019/5285* (2013.01); *A61F 2/013* (2013.01); *C08L 2201/12* (2013.01)

(56) References Cited

U.S. PATENT DOCUMENTS

| | | |
|---|---|---|
| 2001/0001314 A1 | 5/2001 | Davison et al. |
| 2005/0096647 A1 | 5/2005 | Steinke et al. |
| 2006/0089638 A1* | 4/2006 | Carmel et al. ................. 606/41 |
| 2009/0012513 A1 | 1/2009 | Utley et al. |
| 2009/0143705 A1 | 6/2009 | Danek et al. |

FOREIGN PATENT DOCUMENTS

| | | |
|---|---|---|
| EP | 1 790 305 A2 | 5/2007 |
| EP | 1 905 376 A2 | 4/2008 |
| WO | WO 00/51511 | 9/2000 |
| WO | WO 01/22897 | 4/2001 |
| WO | WO 2005/041748 | 5/2005 |
| WO | WO 2009/121017 | 10/2009 |

* cited by examiner

LUMENAL REMODELING DEVICE AND METHODS

RELATED APPLICATION

This application claims the full Paris Convention Priority from, and is a U.S. National Stage entry of PCT/GB2010/051845 filed Nov. 4, 2010; which is based upon GB 0919336.8 filed Nov. 4, 2009, and GB 1010641.7 filed Jun. 24, 2010, each as if fully set forth herein in its entirety.

FIELD

The invention relates to devices and methods for performing percutaneous catheter-based interventional surgery. In particular, the present invention relates to devices and related methods for remodelling the internal surface topography of obstructed hollow anatomical structures such as blood vessels.

BACKGROUND

Many medical conditions can cause the partial or complete occlusion of blood vessels, leading to an insufficient blood supply to tissues and organs. For example, atherosclerosis (also known as arteriosclerotic vascular disease) is a condition in which artery walls thicken and harden due to a build-up of plaque forming fatty materials such as cholesterol. These atheromatous plaques can eventually rupture, with clots forming over the ruptures inside the artery lumen. The clots usually heal and shrink but this process can lead to a narrowing (stenosis) or, worse still, complete closure of the artery. Severe consequences of plaque rupture include aneurysms, myocardial infarction (heart attack) due to a blood clot in the coronary artery and strokes due to a blood clot in an artery to the brain.

Blood clots in veins (venous thromboses) can have equally severe consequences. Superficial venous thromboses generally only cause discomfort but deep venous thromboses (DVTs) that form in the deep veins of the legs or in the pelvic veins can not only block the vein in which they are situated but can also potentially break free from the vein and travel towards the heart and lungs, thereby causing a myocardial infarction or pulmonary embolism.

Tumours are another cause of vascular obstruction, whether benign, pre-malignant or malignant. Hemangiomas, lymphangiomas and glomus tumours are examples of benign tumours that are found in and around blood vessels. Angiosarcomas and Kaposi sarcoma are examples of malignant tumours.

Percutaneous surgical procedures involve insertion of a therapeutic probe, typically a catheter mounted on a guidewire, through an incision made in the skin of the patient. The probe can be guided to a therapeutic site in the body via the circulatory system of arteries and veins, thereby reducing the need to cause more extensive trauma to the patient by adopting more traditional open surgical techniques.

Prior surgical methods for widening the lumen of blood vessels, and in particular for treating atherosclerosis, include balloon angioplasty, laser catheter angioplasty and the use of plaque cutting devices. Balloon angioplasty involves inflating a balloon at the site of blockage in order to compress the atheromatous plaque into the wall of the blood vessel, thus enlarging the lumen of the blood vessel. However, use of this technique involves a high risk of restenosis of the blood vessel due to the reoccurence of arterial plaque. Furthermore, since a relatively high mechanical force is being applied to the plaque there is a risk of plaque dislodgement or of plaque rupture rather than compression, leading to the release of the plaque itself or of plaque contents into the blood stream, which can potentially cause a stroke by embolisation as well as causing other complications. The relatively high mechanical force imparted by the device can also potentially cause the vessel wall itself to rupture.

Laser catheter angioplasty involves inserting a fibre optic cable connected to a laser energy source into the blood vessel and pulsing the laser to vapourise a portion of the plaque. There are several problems associated with laser procedures, most notably the difficulty in locating the fibre optic probe in the correct position and the high risk of blood vessel wall perforation due to the high energy levels used.

Plaque cutting devices use means such as scissors or rotating blades to cut the plaques away from the artery wall. However, the use of such devices runs the risk of damaging and/or perforating the blood vessel wall.

Hence, there exists a need for an improved device which can be used to remodel the internal surface topography of obstructed hollow anatomical structures such as blood vessels of a range of diameters from large to small. In addition, there exists a need for such devices that can be used percutaneously and targeted to sites within the body of a patient that are remote from the operator and which can reliably dilate the lumen of blood vessels at those sites.

SUMMARY

In a first aspect the invention provides a device suitable for remodelling the internal surface of a hollow vessel at least partially occluded by a mass, comprising, an elongate body having a distal end and a proximal end, the distal end comprising a tip portion located at the distal terminus of the body, and at least one heating element located proximally to the tip portion within the distal end; wherein the at least one heating element is configured so as to be greater in dimension proximally than distally and thereby tapers towards the distal end; wherein the at least one heating element is arranged so that it can be deployed outwardly from the body of the device and in so doing exert an expansion force on the hollow vessel; and, wherein the at least one heating element is capable of delivering sufficient energy to remodel the internal surface of the hollow vessel without inducing closure of the hollow vessel.

The at least one heating element may be capable of delivering energy at a rate of up to about 50 Watts, preferably at a rate of up to about 30 Watts, and for a period of up to about 5 minutes.

Furthermore, the at least one heating element may be located on a bladder, which is capable of being inflated so as to expand the at least one heating element. Optionally, the at least one heating element may be integrated with the bladder. The at least one heating element may comprise an electrode with an expandable structure selected from the group consisting of: an umbrella/cone structure; a single helical coil; a double helical coil; and a basket structure.

The at least one heating element may be selected from the group consisting of: a monopolar radiofrequency electrode arrangement; a bipolar radiofrequency electrode arrangement; a plurality of bipolar radiofrequency electrode arrangements; a microwave energy source; an ultrasound energy source; and an electrical current energy source.

Suitably, the at least one heating element may comprise a monopolar radiofrequency electrode arrangement, comprising a first electrode located proximally to the tip portion within the distal end of the elongate body and a second electrode located externally to the patient's body. Alternatively, the at least one heating element may comprise a bipolar radiofrequency electrode arrangement, comprising a first electrode located proximally to the tip portion within the distal end of the elongate body and a second electrode located at a position proximally to the first electrode.

The first electrode of either of these arrangements may be greater in dimension proximally than distally so that it tapers towards the distal end of the elongate body. Furthermore, the first electrode may be arranged so that it can be deployed outwardly from the body of the device and in so doing exert an expansion force on the hollow vessel.

Optionally, the first electrode may be located on a bladder, which is capable of being inflated so as to expand the first electrode. In this instance, the first electrode may comprise an expandable umbrella/cone structure.

The second electrode may be arranged so that it can be deployed outwardly from the body of the device and in so doing exert an expansion force on the hollow vessel. Optionally, the second electrode may be located on a bladder, which is capable of being inflated so as to expand the second electrode. In this instance, the second electrode may comprise an expandable basket structure. Alternatively, the second electrode may comprise an expandable umbrella/cone structure and be configured so as to be greater in dimension distally than proximally and thereby tapers towards its proximal end.

Optionally, the at least one heating element (typically an electrode) comprises one or more apertures. Suitably, the apertures may be configured so as to form an arrangement selected from: one or more transverse slots; one or more longitudinally aligned slots; an array of two or more equally spaced holes; and a grille.

The elongate body of the device may comprise a channel extending along at least a portion of the length of the elongate body for the aspiration of dislodged occluding matter from the lumen of the hollow vessel. Furthermore, the elongate body may comprise at least one port for the infiltration of dislodged occluding matter from the lumen of the hollow vessel into the channel. Suitably, the at least one port is arranged around the circumference of the elongate body.

The elongate body may further comprise a filter located towards the proximal end of the elongate body for the collection of any occluding matter, which has been dislodged from the lumen of the hollow vessel. The filter may comprise an expandable umbrella structure.

Optionally, the elongate body may comprise a guidewire channel extending along at least a portion of the length of the elongate body, the guidewire channel being configured to enable slidable mounting of the device upon a guidewire. Alternatively, the guidewire channel may extend along the entire length of the device to facilitate over-the-wire mounting on a guidewire.

Alternatively, the device may be used in combination with a separate guide catheter (i.e. in the absence of a guidewire).

Suitably, the device may comprise at least one steering member to guide the device into the desired position within the hollow vessel.

At least the distal end of the device may flexible and/or capable of being curved so as to follow the contour of the hollow vessel.

The device may comprise at least one flow sensor to detect the rate of flow of fluid through the hollow vessel. Furthermore, the distal tip portion of the device may comprise a radio-opaque material.

The device may comprise an ultrasound or microwave or electromagnetic transmitter at its distal end to assist with navigation of the device during treatment. Furthermore, the device may be provided with a microwave or RF or iridium-192 radiation source at its distal end for performing local radiotherapy at the site of treatment. Other suitable radio-isotopes may include caesium-137, cobalt-60, iodine-125, palladium-103 and ruthenium-106.

The hollow vessel to be treated may be a blood vessel selected from the group consisting of: an artery; an arteriole; a vein; and a venule. Furthermore, the occluding mass may comprise an atheromatous plaque, a tumour or a thrombosis.

In a second aspect the invention provides a method for remodelling the internal surface of a hollow vessel at a predetermined site within the body of a patient comprising: a) introducing the device of the first aspect of the invention into the hollow vessel; b) directing the device towards the predetermined site within the body of the patient; c) delivering sufficient energy to the hollow vessel so as to remodel the internal surface of the hollow vessel without inducing closure of the hollow vessel; d) monitoring the delivery in step (c); e) ceasing energy delivery when the internal surface of the hollow vessel has been sufficiently remodeled; and, f) withdrawing the device from the hollow vessel.

Step c) of the method may comprise delivering energy at a level of up to about 50 Watts or, typically up to about 30 Watts. Furthermore, energy may be delivered for a period of up to about 5 minutes.

The device may comprise at least one expandable heating element and step c) of the method may further comprise expanding the at least one heating element to exert an expansion force on the hollow vessel. Optionally, the heating element may be pulsed between its unexpanded and expanded configuration so as to avoid adherence of the device to the wall of the hollow vessel during treatment. Alternatively, the device may be continuously rotated and/or advanced back and forth in the hollow vessel so as to avoid adherence of the device to the wall of the hollow vessel during treatment.

The hollow vessel may be a blood vessel selected from the group consisting of: an artery; an arteriole; a vein; and a venule. The methods of the invention also provide for the remodelling of the internal surface of the hollow vessel by inducing an increased level of plasticity in the material located within the vessel at that location, wherein the material includes that selected from the group consisting of: artherosclerotic plaques; thrombosis; calcification; tumour tissue; mucus; stenosis; restenosis; a stent (e.g. collapsed, mislocated or otherwise compromised); or any other occluding matter.

DRAWINGS

The invention is further illustrated by reference to the accompanying drawings in which.

Figure 2A:
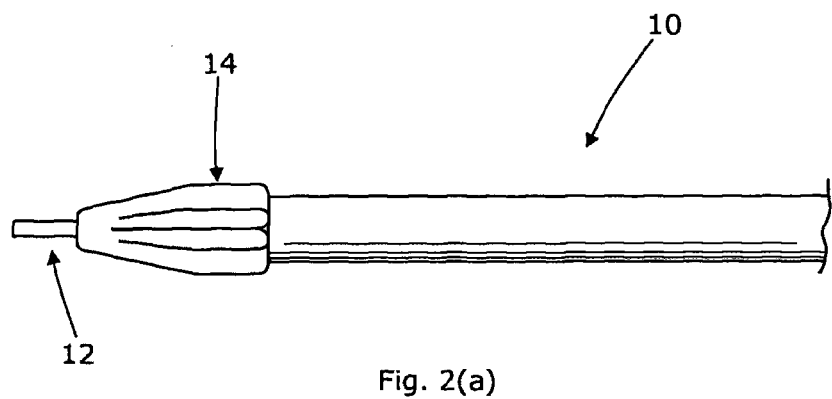
FIG. 2(a) shows a diagrammatic side view of an embodiment of the invention in which the device comprises a monopolar electrode arrangement, shown in the unexpanded configuration.
Figure 3A:
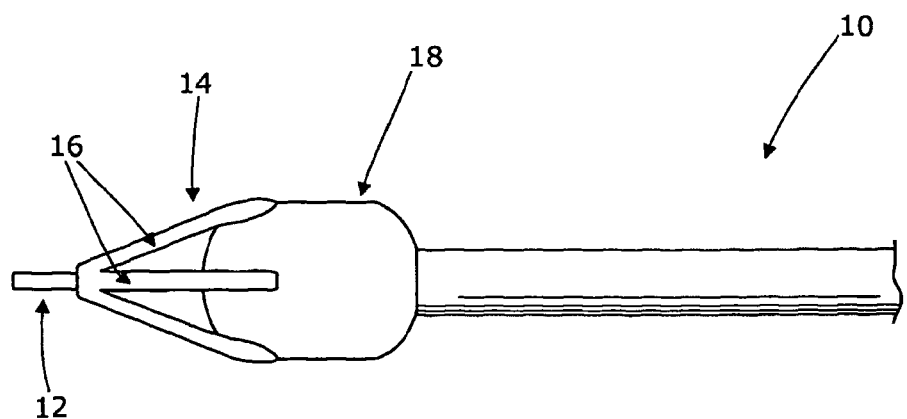
FIG. 3(a) shows a diagrammatic side view of the embodiment of the invention of FIG. 2(a) in which the monopolar electrode is shown in the expanded configuration.
Figure 4A:
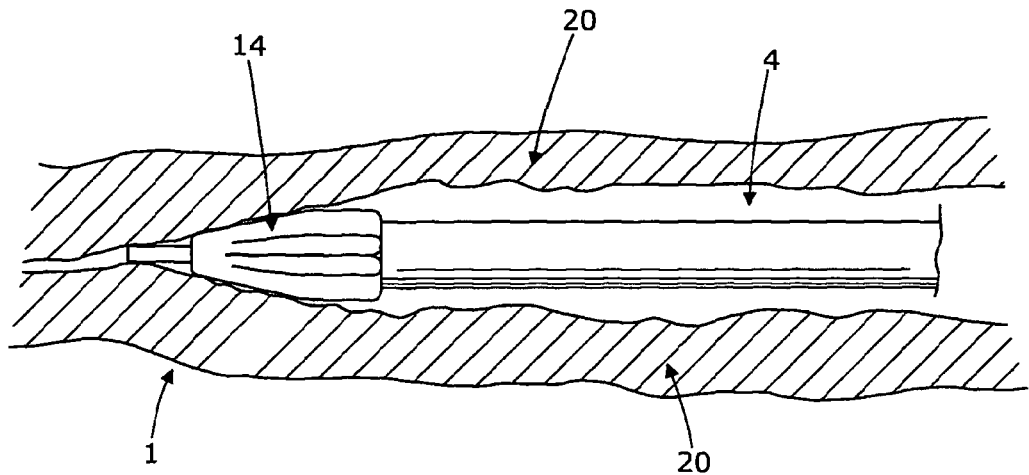
Figure 4B:
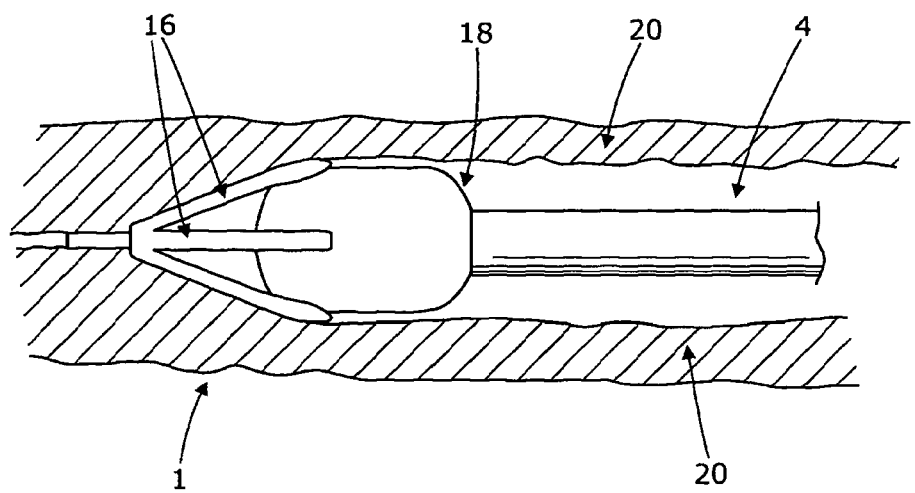

FIG. 4(a) shows a diagrammatic side view of the embodiment of the invention of FIGS. 2(a) and 3(a) in which the device is positioned in an occluded blood vessel and the monopolar electrode is shown in the unexpanded configuration. FIG. 4(b) shows a diagrammatic side view of the embodiment of the invention of FIGS. 2(a) and 3(a) in which the device is positioned in an occluded blood vessel and the monopolar electrode is shown in the expanded configuration, thereby remodelling the internal surface topography of the vessel wall.

Figure 2B:
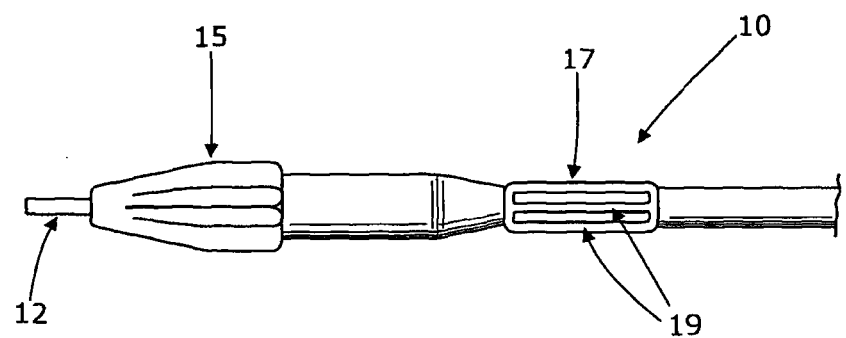
FIG. 2(b) shows a diagrammatic side view of an embodiment of the invention in which the device comprises a bipolar electrode arrangement, shown in the unexpanded configuration.
Figure 3B:
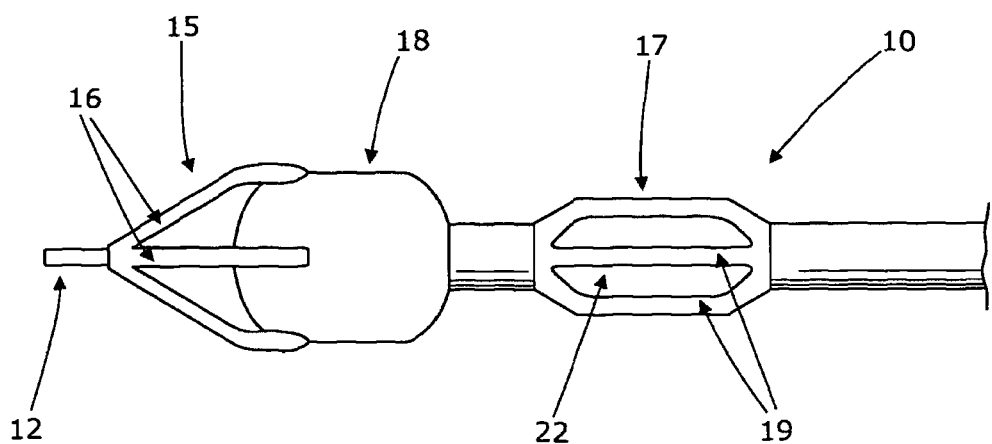
FIG. 3(b) shows a diagrammatic side view of the embodiment of the invention of FIG. 2(b) in which the bipolar electrodes are shown in the expanded configuration.
Figure 5A:
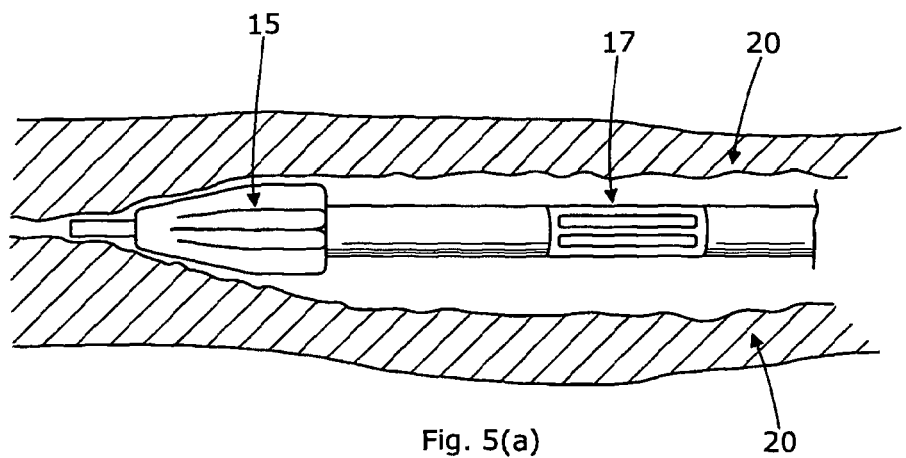
Figure 5B:
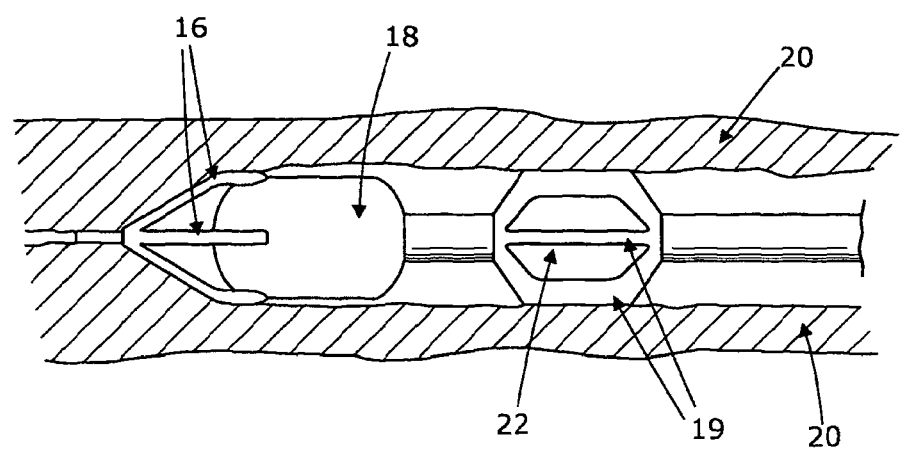

FIG. 5(a) shows a diagrammatic side view of the embodiment of the invention of FIGS. 2(b) and 3(b) in which the device is positioned in an occluded blood vessel and the electrodes are shown in the unexpanded configuration. FIG. 5(b) shows a diagrammatic side view of the embodiment of the invention of FIGS. 2(b) and 3(b) in which the device is positioned in an occluded blood vessel and the electrodes are shown in the expanded configuration, thereby remodelling the internal surface topography of the vessel wall.

Figure 6:
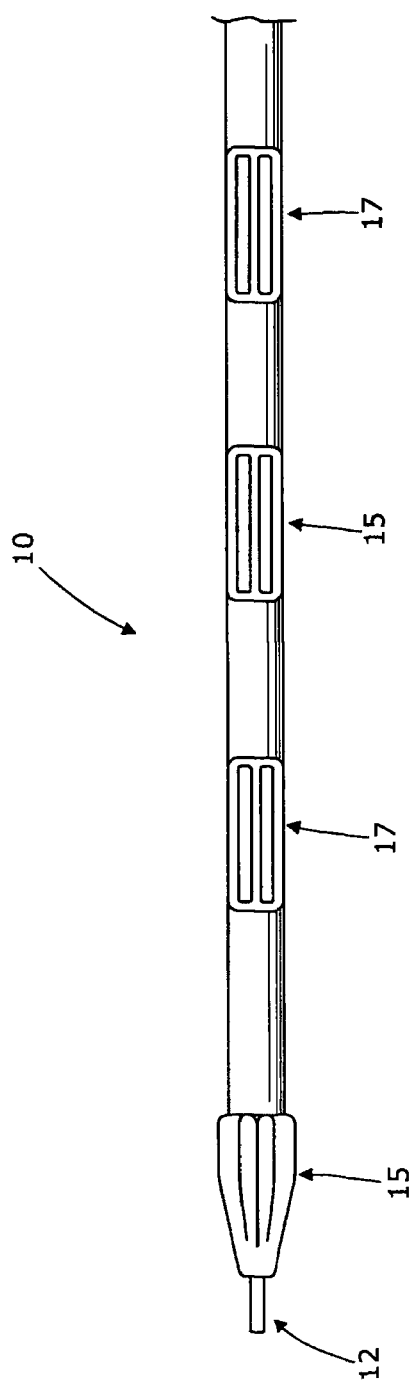

FIG. 6 shows a diagrammatic side view of an embodiment of the invention in which the device comprises an array of bipolar electrode arrangements, shown in the unexpanded configuration.

Figure 7A:
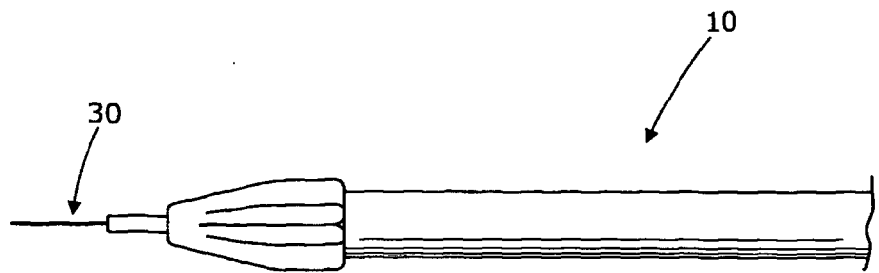
Figure 7B:
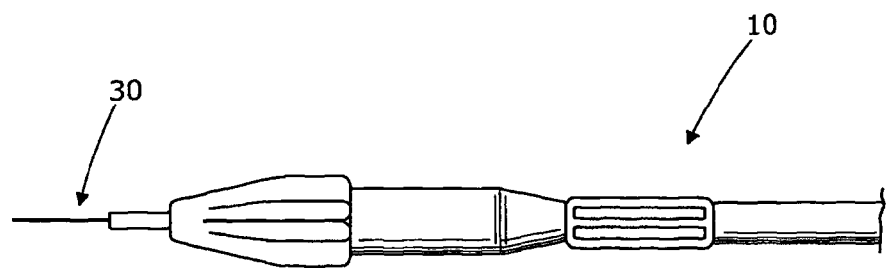
Figure 7C:
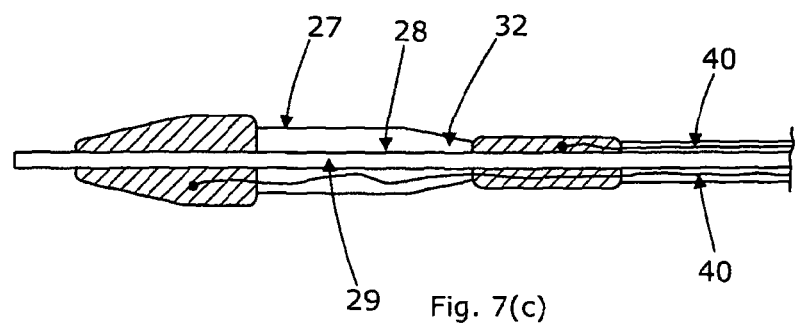

FIG. 7(a) shows a diagrammatic side view of an embodiment of the invention in which the device comprises a monopolar electrode arrangement and is deployed over a flexible guidewire. FIG. 7(b) shows a diagrammatic side view of an embodiment of the invention in which the device comprises a bipolar electrode arrangement and is deployed over a flexible guidewire. FIG. 7(c) shows a diagrammatic sectional view of an embodiment of the invention in which the device comprises a bipolar electrode arrangement and the annular chamber between the inner wall and the outer wall of the catheter houses electrical conductors or leads that allow connection of the external RF energy source to the bipolar electrodes.

Figure 8:
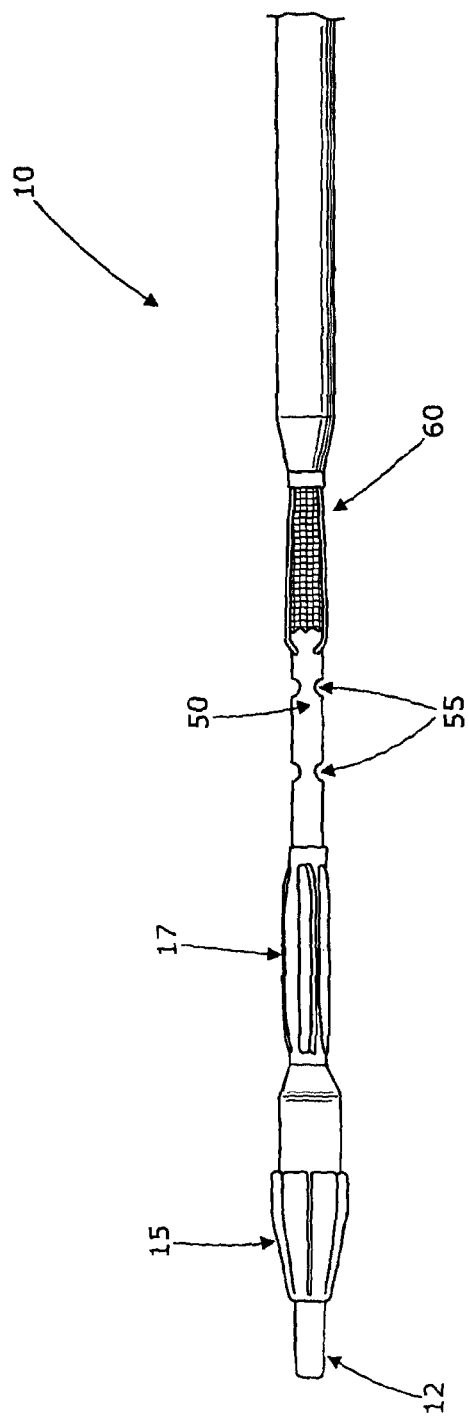

FIG. 8 shows a diagrammatic side view of an embodiment of the invention in which the device additionally comprises an aspiration channel, for the aspiration of loose occluding matter from the lumen of the hollow vessel, and a filter cage located towards the proximal end of the device. The electrodes and the filter cage are shown in the unexpanded configuration.

Figure 9:
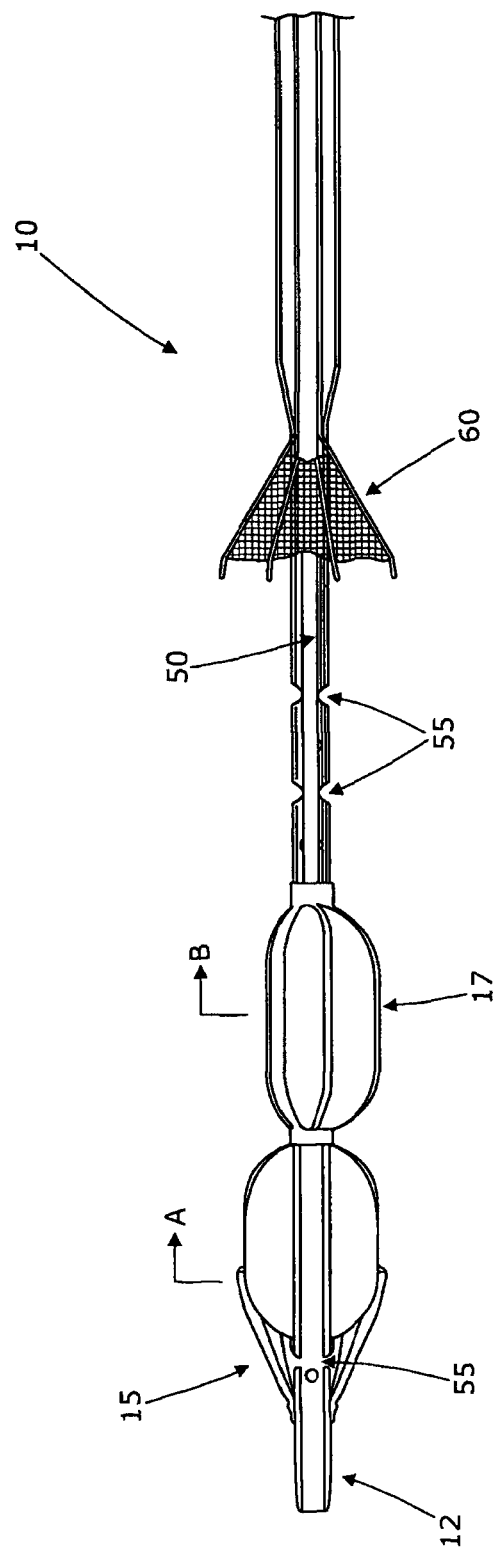

FIG. 9 shows a diagrammatic side sectional view of the embodiment of FIG. 8, with the electrodes and the filter cage in the expanded configuration.

Figure 10:
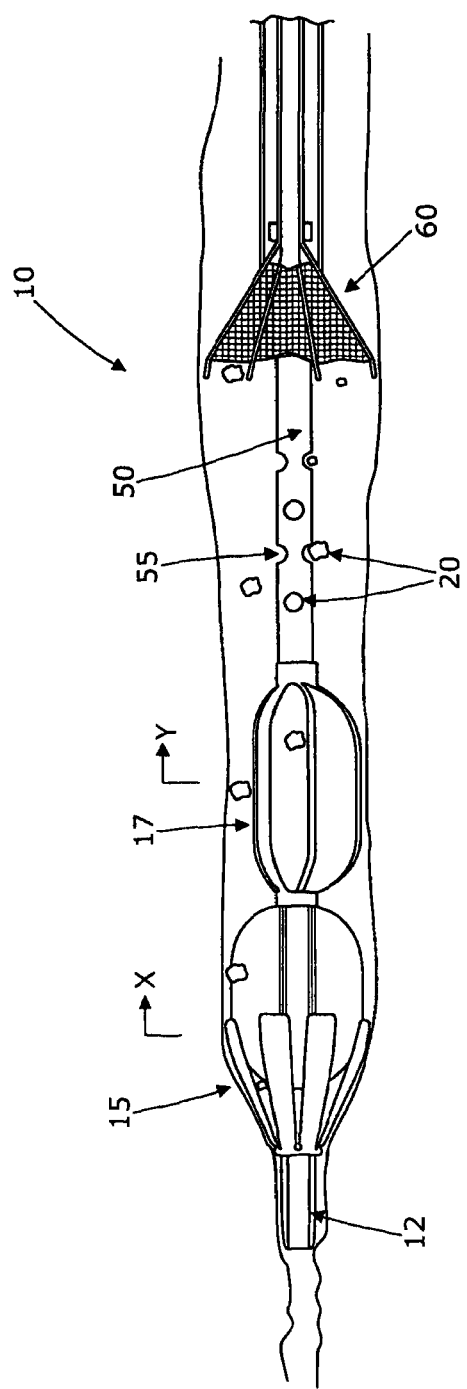

FIG. 10 shows a diagrammatic side view of the embodiment of FIGS. 8 and 9, showing loose particulates being infiltrated through the aspiration channel and collected by the filter cage.

Figure 11A:
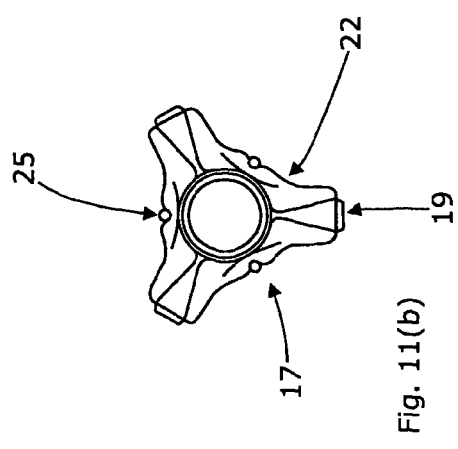
Figure 11B:
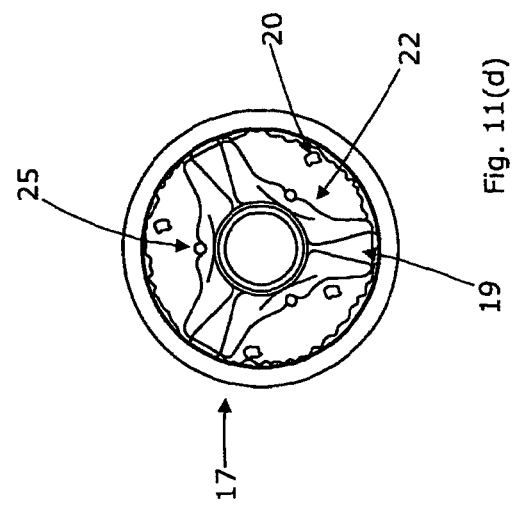
Figure 11C:
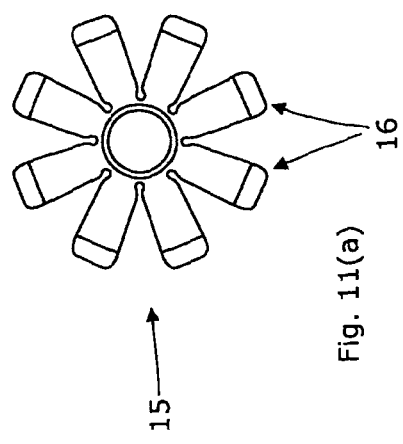
Figure 11D:
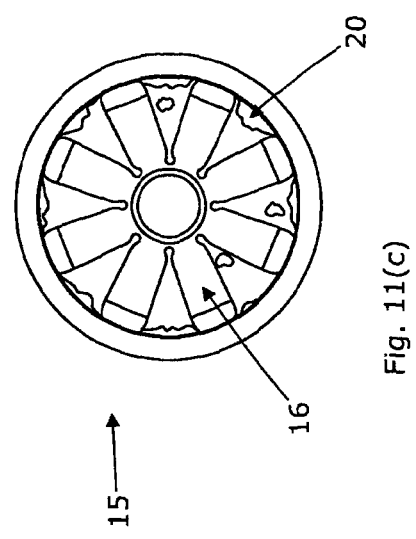

FIG. 11(a) shows an axial view of an expanded monopolar electrode or distal electrode of a bipolar electrode arrangement of the invention along line A in FIG. 9. FIG. 11(b) shows an axial view of an expanded proximal electrode of a bipolar electrode arrangement of the invention along line B in FIG. 9. FIG. 11(c) shows an axial view of an expanded monopolar electrode or distal electrode of a bipolar electrode arrangement of the invention along line X in FIG. 10 in situ in an occluded vessel with loose particulates passing between the electrode arms. FIG. 11(d) shows an axial view of an expanded proximal electrode of a bipolar electrode arrangement of the invention along line Y in FIG. 10 in situ in an occluded vessel with loose particulates passing between the electrode arms.

Figure 12:
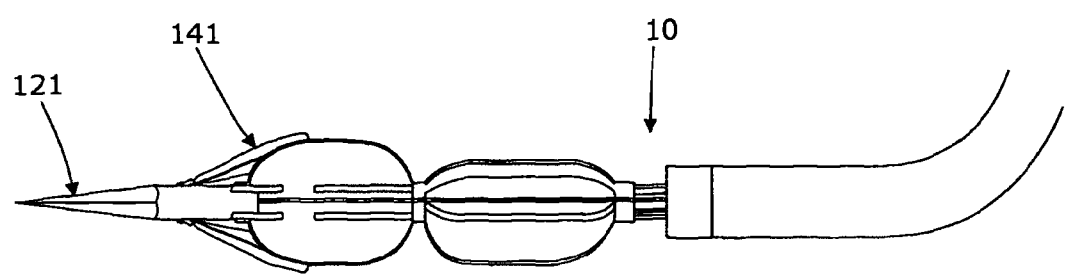

FIG. 12 shows a side view of an embodiment of the invention in which the tip is formed as a trocar and where the device is adapted for deployment within a guide catheter.

Figure 13A:
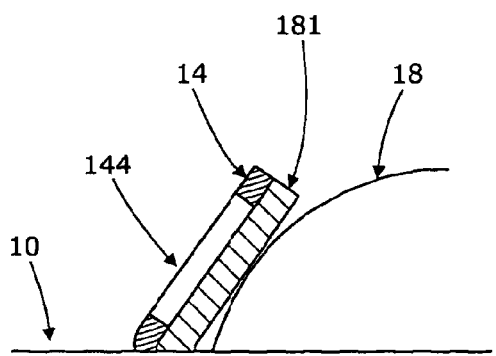
Figure 13B:
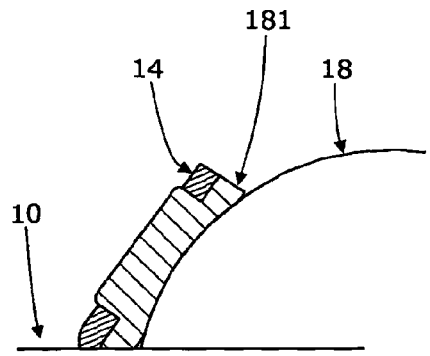

FIG. 13 (a) shows a longitudinal cross section view of the interaction of the balloon and the electrode in an embodiment of the invention. In particular, a spacer member or washer is shown located proximally to the electrode intervening the electrode and balloon. In FIG. 13(b) the balloon is inflated so as to cause deformation of the washer, which bears upon the electrode and extends outwardly through an aperture in the central region of the electrode. FIG. 13 (c) shows an electrode of the invention in a quadrifoliate arrangement, each arm of the electrode bears a different configuration of apertures by way of example. Also shown is a quadrifoliate washer that supports the overlaid electrode. A cross section view along line C-C with electrode placed adjacent to the washer is also provided.

DETAILED DESCRIPTION

Unless stated otherwise the terms used herein have the same meanings as those understood by a person of appropriate skill in the art. All cited documents are herein incorporated by reference in their entirety.

Figure 1A:
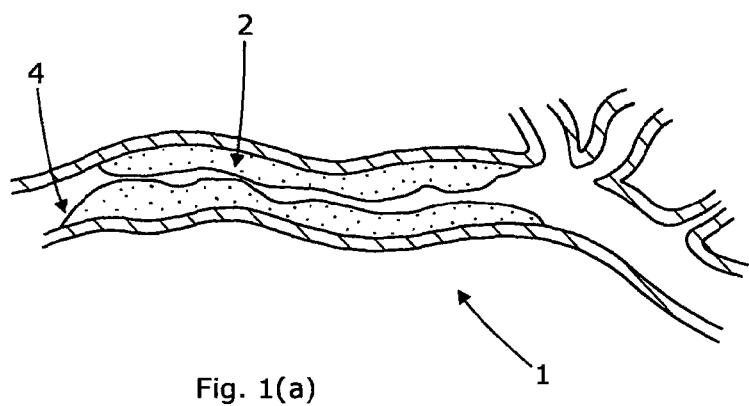
FIG. 1(a) shows an atherosclerotic blood vessel, which is partially obstructed due to atheromatous plaques.
Figure 1B:
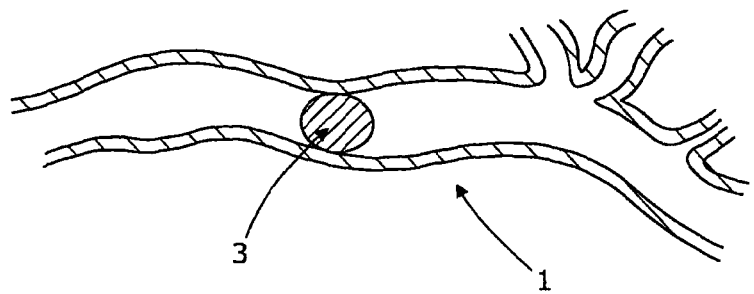
FIG. 1(b) shows a blood vessel, which is completely occluded with a tumour or blood clot.

FIGS. 1(a) and (b) illustrate how a blood vessel may be occluded, either partially or fully. Specifically, FIG. 1(a) shows an atherosclerotic blood vessel 1 with thickened walls due to the formation and build-up of atheromatous plaques 2. The plaques 2 narrow the blood vessel lumen 4 so that the passage of blood through the vessel 1 is restricted, or in some cases completely stopped. FIG. 1(b) shows how a blood vessel 1 can be occluded by a blood clot or tumour 3.

A first embodiment of the invention is shown in FIG. 2(a) and FIG. 3(a). The device 10 comprises an elongate catheter including a proximal end (not shown), where control of the device is administered by the user, and a tip portion 12 at its distal end. The distal end of the catheter is typically located at the site within the body of the patient where therapy is to be administered. The tip portion 12 is inert and can comprise a radio-opaque material to enhance the ability to visualise the tip in vivo and direct therapy to the correct location. The tip portion 12 may be substantially blunt ended or in one embodiment of the invention the tip 12 may be formed into a sharp point so as to form a trocar 121 (see FIG. 12) and has an electrode 141 adjacent thereto. The trocar 121 may be formed from a partially elastic or deformable material (e.g. a silicone rubber) so as not to cause penetrative damage to the vessel walls. Located proximally to the tip portion 12 at the distal end of the elongate body is a single radiofrequency (RF) electrode (heating element) 14 (a monopolar electrode arrangement). A grounding pad in contact with the patient's body (not shown) provides the other electrode polarity and completes the RF circuit. The monopolar electrode 14 and the grounding pad are connected to opposite polarities of an RF energy source. When the device 10 is in use, RF current flows between the monopolar electrode 14 and the grounding pad, resulting in a local heating zone around the monopolar electrode 14, which is used to assist in remodelling (for example, unblocking and/or widening) the lumen of the vessel (for example, a blood vessel).

In one embodiment of the invention, the monopolar electrode 14 is substantially cylindrical in cross-section and tapers from its proximal end towards its distal end, i.e. the electrode 14 narrows towards its distal end such that the distal end of the electrode 14 is smaller in diameter than the proximal end of the electrode 14. This tapered electrode configuration enables the distal end of the device 10 to be advanced through the lumen of a narrowed vessel towards and into the site of obstruction (see FIG. 4(a), for example).

As shown in FIG. 2(a), the tapering of the electrode does not begin at the most proximal point of the electrode, rather it begins part of the way along the length of the electrode, suitably about a quarter or a third of the way along the length of the electrode from the proximal end. This provides the proximal end of the electrode with a substantially flat cylindrical surface, when the electrode is in an unexpanded configuration, that approximately parallels the wall of the vessel to be treated and which helps to compress the occluding matter into the wall of the vessel such that the resultant remodeled lumen forms an approximately cylindrical conduit. The angle of tapering of the electrode from its proximal end to its distal end, relative to the longitudinal axis of the device 10, is between about 20° and about 60°, suitably between about 35° and about 50°, most suitably about 45°, when the electrode is in an unexpanded configuration. When the electrode is expanded, see for example FIG. 3(a) and FIG. 9(a), the angle of tapering of the electrode from its proximal end to its distal end increases relative to the longitudinal axis of the device.

In an alternative embodiment of the invention (not shown), tapering of the electrode may begin at the most proximal point of the electrode such that the electrode is tapered along its entire length from its proximal end to its distal end.

As is shown most clearly in FIG. 3(a) and FIG. 11(a), and as described above, the monopolar electrode 14 takes the form of an expandable umbrella frustoconical or cone shaped structure comprising a plurality of arms or spokes or leaves 16. In a specific embodiment of the invention, the electrode comprises a plurality of arms that extend proximally from a distally located collar. Alternative forms of expandable structures may include a single helical coil, a double helical coil, and a basket/cage type structure, amongst others. The cone shaped monopolar electrode 14 may be pre-stressed or sprung to assist with its expansion. Hence, in use the arms pivot outwardly about the distal attachment point when expansion of the electrode occurs. Importantly, when the electrode 14 is in the expanded configuration the interstices between adjacent arms 16 may permit the continued flow of fluid, such as blood, through the vessel so that the device itself does not cause obstruction of fluid flow and facilitates cooling of the occluding material as to reduce the risk of thermal ablation of the surrounding vessel walls and tissue. Typically, the electrode 14 comprises between three and nine arms, suitably six arms, and most suitably three arms in order to maximise the flow of fluid past the electrode 14. The number of arms controls the available surface area contact the electrode 14 has with the internal surface of the vessel wall and, thus, the amount of energy transmitted thereto. The greater the number of arms, the greater the area of contact between the electrode 14 and the vessel wall and, therefore, the greater the remodelling effect of the device.

In one embodiment of the invention, the electrode 14 can be deployed into the expanded configuration using an inflatable bladder or balloon 18, which is located at the distal end of the device 10 beneath the electrode 14 and extends beyond the proximal end of the electrode 14 so as to help expand the diameter of the lumen of the vessel to be treated (see FIG. 3(a)). The balloon 18 is typically constructed from silicone, or other suitable elastic biocompatible materials. The balloon 18 can be inflated and deflated by injecting fluid (which may be a liquid, such as saline, or gas) using techniques known from percutaneous angioplasty. For example, the device may comprise a channel that carries the fluid used to inflate and deflate the balloon 18 from an external source. In a specific embodiment, the balloon 18 is inflated via a constant flow of fluid. In this way the fluid used to expand and deploy the balloon 18 also serves to irrigate the bladder thereby acting as a local coolant, especially in the region of the balloon 18 directly adjacent to the electrode 14. Restriction of the level of outflow of the fluid from the balloon 18 would enable an increase of pressure within the balloon 18 in order to effect inflation of the balloon 18. In a further embodiment of the invention as shown in FIG. 13(a), the electrode 14 is spaced apart from the balloon 18 via a spacer member such as a washer 181 which may serve to provide additional support for the overlying electrode 14 as well as heat shielding for the material that is used to form the outer skin of the balloon 18. The washer 181 is suitably made from silicone gel, silicone rubber or any other approved and compatible polymeric material known to the skilled artisan.

Alternatively, the electrode 14 can be deployed into the expanded configuration mechanically via one or more actuation members (such as wires) incorporated within the device and controlled remotely by the user.

Typically, the devices of the invention are operated according to three main phases of therapy: an insertion phase, a therapy phase and a removal phase. The insertion phase includes the percutaneous insertion of the device 10 (optionally preceded by the insertion of a guidewire, if required) and the location of the device 10 to the site where therapy is to be administered. The therapy phase includes the steps of deploying the monopolar electrode 14 and administering sufficient energy to remodel the internal surface topography of the hollow vessel without inducing closure of the hollow vessel through thermal ablation of the surrounding tissue. The removal phase includes the retraction of the electrode 14 and withdrawal of the device 10 (and the guidewire, if used) from the site of remodelling, usually back along the initial insertion route.

As shown in FIGS. 4(a) and 4(b), during the therapy phase, the balloon 18 is inflated to deploy the monopolar electrode 14 outwardly from the body of the device 10 such that it comes into contact with and exerts an expansion force on the occluding material 20, which is for example, an atheromatous plaque, a thrombosis or a tumour. At the same time, the RF current is activated so that a controlled heating zone is formed around the electrode 14. The combination of heat and mechanical force allows the device 10 to effectively melt/soften and compress the occluding matter 20 into the wall of the vessel 1 so as to remodel (for example, widen) the lumen 4 of the vessel 1. When the occluding material 20 is an atheromatous plaque, for example, the combination of heat and mechanical force means that the plaque is far less likely to rupture and release its contents into the blood stream than if mechanical force alone is used, such as via traditional balloon angioplasty. This is because the gentle heating action encourages the plaque to plasticise in a controlled manner and the immediate compression by the electrode itself then melds and compresses the plaque contents into the vessel wall.

The level of energy delivered by the electrode 14 is sufficient to allow remodelling of the internal surface topography of the hollow vessel 1. However, it is not so high so as to induce closure of the hollow vessel 1 through extensive denaturation of the intima or surrounding tissue. In certain embodiments, the application of RF energy has been shown to cause partial degeneration of muscle fibres so that the vessel wall can be deformed. The expansion force exerted by the electrode 14 dilates the lumen of the vessel 1. The fact that the tip portion 12 of the device 10 is inert and the electrode 14 is located proximally to the tip portion 12 helps to ensure that the closure of the vessel 1 does not occur during heating. The user of the device 10 can decide how long to apply the RF current for and at which energy level. This choice will be in part dictated by the size of the occluded vessel and in part by the size of the occlusion itself. Typically, for a small vessel such as a vein or an arteriole, the level of energy delivered will be up to about 5 Watts, suitably in the range of about 0.1 Watt to about 3 Watts, more suitably about 0.5 Watts to about 1.5 Watts, and yet more suitably about 1 Watt, for about 10 seconds to about 3 minutes, suitably about 30 seconds to about 2 minutes, and more suitably about 60 seconds. For a larger vessel such as an artery, the typical level of energy delivered may be up to about 50 Watts, suitably up to about 40 Watts, more suitably up to about 30 Watts, and yet more suitably in the range of about 20 Watts to about 30 Watts, for up to about 5 minutes, suitably up to about 4 minutes, and more suitably up to about 3 minutes. Alternative power levels and timings will be appropriate for other non-cardiovascular vessels such as bronchioles, bile ducts and fallopian tubes. Likewise, power levels may be altered dependent upon the nature of the occlusive material. It is within the remit of the skilled addressee to trial suitable power levels on cadaveric or animal material in advance of use in surgery.

In use, the device 10 is advanced along the occluded lumen 4, aided by the tapered configuration of the electrode 14, and softens and remodels the heated occluding matter 20 into the vessel wall. As the occluding matter 20 cools it adopts the compressed position. When the lumen 4 of the vessel 1 has been sufficiently widened to restore effective flow, the energy delivery is ceased and the electrode 14 is retracted to its unexpanded configuration. The device 10 is then withdrawn from the vessel 1.

A second embodiment of the invention is shown in FIG. 2(b) and FIG. 3(b). The device 10 is similar to the device of the first embodiment of the invention except that it comprises a bipolar RF electrode arrangement, including a distal electrode 15 and a proximal electrode 17 at the distal end of the device. The distal electrode 15 is similar to the monopolar electrode 14 of the device of the first embodiment of the invention, i.e. it is tapered from its proximal end towards its distal end and may include an expandable umbrella/cone structure. The distal 15 and proximal 17 electrodes are connected to opposite polarities of an RF energy source. In use, RF current flows between the electrodes and causes heating and, thus, depending upon the distance between the electrodes can result in a controlled heating zone between the electrodes which is used to assist in remodelling the lumen of the vessel.

The proximal electrode 17 is substantially cylindrical in cross-section and comprises an expandable basket/cage type structure comprising a plurality of arms or spokes 19. The arms or spokes 19, as shown in FIG. 2(b) and FIG. 3(b), are linear in configuration and extend along the electrode 17 between the distal end and the proximal end of the electrode 17. In an alternative embodiment of the invention (not shown), the arms or spokes 19 may take the form of a single or double helical coil. When in the expanded configuration, as shown for example in FIG. 3(b) and FIG. 9, the arms or spokes 19 of the proximal electrode 17 are straight along the majority of their length and run axially along the device 10, but are tapered at their ends towards the proximal and distal termini of the electrode 17. The tapering of the ends of the arms or spokes 19 towards the distal and proximal ends of the electrode 17, when the electrode 17 is in the expanded configuration, helps to provide a smooth electrode surface for remodelling the lumen of the vessel that is to be treated.

As per the distal electrode 15, the interstices between adjacent arms/spokes 19 of the proximal electrode 17 allow for the continued flow of fluid, such as blood, through the vessel so that the device 10 itself does not cause obstruction of fluid flow. Typically, the proximal electrode 17 comprises between three and nine arms, suitably between three and six arms, most suitably three arms in order to maximise the flow of fluid past the electrode. In one embodiment of the invention, three arms are selected (e.g. a trifoliate arrangement) so as to minimise the contact area between the proximal electrode 17 and the internal vessel wall so as to reduce the likelihood of the proximal electrode 17 adhering to the vessel wall itself during use.

In one embodiment of the invention, the diameter of the proximal electrode 17 is substantially constant along its length when in the unexpanded and expanded configurations. When both the distal electrode 15 and the proximal electrode 17 are in the expanded configuration, the diameter of the proximal electrode 17 does not exceed the diameter of the distal electrode 15, i.e. the proximal electrode 17 may be equal to or smaller than the diameter of the distal electrode 15 when in the expanded configuration. FIG. 3(b) shows the proximal electrode 17 having a smaller diameter than the distal electrode 15, whereas FIGS. 5(a) and (b) show the proximal electrode 17 having the same diameter as the distal electrode 15.

In another embodiment of the invention (not shown), the distal electrode 15 tapers from its proximal end towards its distal end (as previously described) and the proximal electrode 17 tapers from its distal end to its proximal end, i.e. the proximal electrode 17 tapers in the opposite direction to the distal electrode 15. This dual oppositely tapered electrode configuration enables the device to be used in both directions in the vessel, i.e. in both the forwards direction (as previously described) and the backwards direction. For example, the device can be advanced through the lumen of a narrowed vessel towards and past the site of obstruction, whereupon the electrodes are deployed, then the device can be reversed along the vessel to remodel the internal surface structure from the opposite direction using the tapered proximal electrode 17.

The proximal electrode 17 can be deployed into the expanded configuration using an inflatable bladder or balloon 22 as per the distal electrode 15 described above. In order to further maximise fluid (such as blood) flow around the proximal electrode 17, the balloon 22 may be configured so as not to have a cylindrical cross-section. This can be achieved by using a multi-lobed balloon, suitably a tri-lobed balloon (see FIG. 11(b)). The balloon 22 is divided into lobes using retaining members 25 which extend along the length of the balloon 22 and are anchored at either end of the balloon 22, thereby constraining the expansion of the balloon 22 when inflated. An alternative way of achieving a non-cylindrical cross-section is to use multiple balloons positioned around the circumference of the device 10, since the gaps between adjacent balloons will permit fluid flow past the device and through the vessel. This non-cylindrical cross-section balloon configuration can also be applied to balloon 18, which is used to expand the distal electrode 15.

Figure 13C:
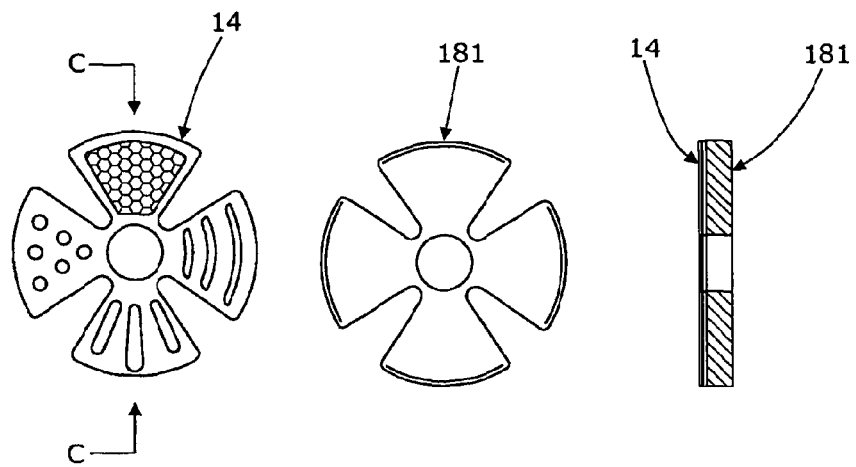

Alternative configurations of the electrodes 14-17 are shown in FIG. 13(c). The arms of the electrodes may comprise one or more apertures that influence the power distribution, heating effects and/or serve to reduce adherence between the occlusive material and the electrode when in use (so-called "tissue-stick"). The exemplary electrode 14 shown in FIG. 13 (c) shows four aperture patterns that are suitable for use in various embodiments of the present invention. A first arrangement comprises a grille pattern that serves to minimise electrode contact with the walls of the vessel. Other arrangements include an array of grooves, slots or holes that extend axially about or longitudinally along the electrode arm and may also serve as cutting or abrading surfaces to assist in remodelling the interior surface of the vessel. The electrode configurations are suitably applied using laser cutting, punching or etching techniques known in the art. It will be understood that an electrode 14 may suitably comprise all of the same pattern on each arm of the electrode 14 or a combination of different patterns. Likewise, as described above, the electrodes of the invention may include other electrode arrangements with different numbers of arms some, none or all of which may comprise the exemplary aperture patterns. It is optional for the electrode 14 to be used in combination with an underlying and suitably configured washer 181, which is also shown in FIG. 13 (*c*).

In use, as per the first embodiment of the invention and as shown in FIGS. 5(*a*) and (*b*), the balloon 18 associated with the distal electrode 15 is inflated to deploy the distal electrode 15 outwardly from the body of the device 10 such that it comes into contact with and exerts an expansion force on the occluding material 20. At the same time, the RF current is activated so that a controlled heating zone is formed between the distal 15 and proximal 17 electrodes. The balloon 22 associated with the proximal electrode 17 is also inflated so as to deploy the proximal electrode 17 outwards from the body of the device 10. The expanded proximal electrode 17 provides an additional heating path and expansion force so as to further remodel and compress the occluding material 20 into the vessel wall. It is not absolutely necessary for balloon 22 to be expanded in addition to balloon 18, the proximal electrode 17 can simply be activated to emit heat, but expansion of balloon 22 it will help to provide a further expansion force on the vessel wall and to improve remodelling of the lumen of the vessel.

In an alternative embodiment of the invention as shown in FIG. 6, the device 10 may comprise an array of expandable bipolar electrode arrangements (comprising distal electrodes 15 and proximal electrodes 17) so that thermally assisted remodelling (for example, expansion) of the vessel lumen can take place along an increased proportion of the vessel at a single time. Only the most distal electrode 15 nearest the tip portion 12 is arranged so as to comprise the tapered expandable umbrella/cone structure as previously described. The remaining electrodes positioned proximally to the most distal electrode nearest the tip portion 12 comprise the expandable basket/cage type structure as previously described. However, in a further embodiment of the invention, the most proximal electrode 17 nearest the proximal end of the device 10 also comprises the tapered expandable umbrella/cone structure as previously described and tapers from its distal end to its proximal end, i.e. the most proximal electrode 17 tapers in the opposite direction to the most distal electrode 15 so as to enable the device 10 to be used in both directions in the vessel.

In yet a further embodiment of the invention (not shown), the device may comprise an array of bipolar electrodes, at least one of which is expandable. For example, the most distal electrode nearest the tip portion may be expandable but the electrodes positioned proximally to the most distal electrode nearest the tip portion may not be expandable.

In another embodiment of the invention (not shown), the device comprises a monopolar electrode arrangement in which the monopolar electrode is substantially cylindrical in cross-section and comprises an expandable basket/cage type structure comprising a plurality of arms or spokes. The arms/spokes may be straight or may take the form of a single or double helical coil.

In yet another embodiment of the invention (not shown), the device comprises a bipolar electrode arrangement in which the distal electrode is substantially cylindrical in cross-section and comprises an expandable basket/cage type structure comprising a plurality of arms or spokes. The arms/spokes may be straight or may take the form of a single or double helical coil.

In a further embodiment of the invention as shown in FIGS. 7(*a*) and (*b*), the device 10 is optionally deployed over a flexible guidewire 30. The device 10 comprises an elongate catheter body that is constructed with an outer wall 27 and an inner wall 28, see FIG. 7(*c*). The lumen 29 defined by the inner wall 28 will accept a guidewire 30 so that the device 10 may be loaded over a pre-located guidewire 30 and directed to the site in the patient's body requiring therapy. The lumen 29 may extend substantially along the entire length of the device 10 (thereby facilitating an over-the-wire mounting on the guidewire) or along only a portion of the device 10 (thereby facilitating a monorail mounting on the guidewire).

The annular chamber 32 between the inner wall 28 and the outer wall 27 houses conductors or leads 40 that allow connection of the external RF source to the monopolar and bipolar electrodes, (see FIG. 7(*c*) for a bipolar electrode arrangement with conductors 40). In embodiments of the invention where the device 10 has no guidewire channel, the conductors or leads 40 for connection of the external RF energy source to the monopolar and bipolar electrodes are still located within the body of the device.

In yet another embodiment of the invention (not shown), the device is guided to the site of treatment by at least one steering member. Typically, a plurality of steering members extend longitudinally along the body of the device.

In an alternative embodiment of the invention (not shown), the expandable monopolar or bipolar electrodes (as described in previous embodiments of the invention) are located on a guidewire. The associated catheter is provided solely with at least one expansion means (such as an expandable bladder or balloon) to further assist with remodelling the lumen of the vessel. Such an arrangement may be suitable in vessels that are particularly small, for instance, where the vessel diameter is less than 2 mm, or even less than 1 mm. In very narrow vessels it can be difficult to accurately deploy a catheter over the guidewire. Small vessel diameters are not uncommon in cerebrovascular indications and in oncology.

In one embodiment of the invention (not shown), at least the distal end of the device is flexible and/or is capable of being curved so as to follow the natural curvature of the vessel lumen. For example, steering members located within the device may be used to control curvature of the distal end of the device. Alternatively, at least the distal end of the device can be curved by using a heat formed sprung wire or Nitinol comprised within the elongate body.

In a further embodiment of the invention as shown in FIGS. 8 to 10, the device 10 includes an aspiration channel 50 for suctioning occluding matter 20 released from the lumen of the hollow vessel during operation of the device. FIGS. 8 to 10 show a device 10 having a bipolar electrode arrangement and an aspiration channel 50 extending the length of the device 10 from the inert distal tip portion 12 through to the proximal end of the device 10. The aspiration channel 50 has entry points or ports 55 arranged about the circumference of the body of the device 10. These ports 55 are suitably located distally adjacent to the distal electrode 15 (see FIG. 9) and also proximally adjacent to the proximal electrode 17. Alternative arrangements of entry ports 55 are contemplated, for example, the entry ports 55 may just be located proximally to the proximal electrode 17.

The device 10 may further comprise a filter 60 (for example, a filter cage) located towards the proximal end of the elongate body of the device 10 for the collection of occluding matter 20 which has come loose from the wall of the vessel whilst the electrodes are remodelling and compressing the occluding material 20. In one embodiment of the invention, the filter 60 is in the form of an expandable webbed umbrella structure as shown in FIGS. 9 and 10 (for example, the solid arms of the filter are interspersed by mesh to catch particulates), which is able to expand outwardly across the entire circumference of the lumen of the vessel and thereby intercept any loose material 20, whilst still allowing fluid (such as blood) to flow past the device 10 along the vessel. The filter 60 may be present in addition to or instead of the aspiration channel 50.

During the therapy phase, it is possible (although unlikely when using the thermally assisted mechanical expansion technique of the invention) that occluding matter may come loose from the vessel wall and enter the blood stream. This matter may include fatty particulates/deposits from atheromatous plaques or pieces of tumours or thromboses. In certain instances, it can be important to catch these loose particulates, otherwise they can potentially cause a stroke or myocardial infarction, for example. Therefore, during the therapy phase (see FIG. 10 in particular) the filter 60 can be expanded and suction applied to the aspiration channel 50, as and when necessary, whilst the electrodes are remodelling and compressing the occluding material into the wall of the vessel. This ensures that any loose material 20 is infiltrated through the entry ports 55 into the aspiration channel 50 or are retained within the filter 60, and are not liberated into the wider blood stream. The filtered blood can be transfused back to the patient or retained for histological analysis. FIGS. 11(c) and (d) show how loose particulates flow between the arms 16 of the distal electrode 15 and the arms 19 of the proximal electrode 17.

It is also possible for devices of the invention having a monopolar electrode arrangement or an array of bipolar electrode arrangements to be provided with an aspiration channel. Furthermore, an aspiration channel may be provided together with a guidewire channel. It is also possible for substances, including drugs, to be administered to the site of treatment through the guidewire channel and/or the aspiration channel.

In an alternative arrangement (not shown), the aspiration channel may extend along only a portion of the length of the device from a position proximal to the monopolar/distal electrode through towards the proximal end of the device.

An issue that can potentially arise during treatment is sticking/adherence of one or more of the electrodes of the device to the tissue of the vessel wall. As previously discussed, one way of avoiding or minimising this problem is to use an electrode that comprises a number of individual arms separated by spaces rather than using a complete electrode, so as to minimise the contact surface area between the electrode and the internal vessel wall. Suitably, a minimum of three electrode arms has been found to be suitable for applying sufficient heat so as to effectively remodel the lumen of the vessel and to minimise adherence of the electrode to the vessel wall itself. The electrode can comprise an increased number of arms depending on the size/thickness of the occlusion.

An alternative way of reducing sticking/adherence of one or more of the electrodes of the device to the tissue of the internal vessel wall is to "pulse" or oscillate the electrode during treatment, i.e. to move the electrode slightly between its unexpanded and expanded configurations. Where the electrode is expanded using a balloon, this can be done either by rapidly inflating and deflating the balloon 18 located beneath the distal electrode 14 and/or by rapidly inflating and deflating the balloon 22 beneath the proximal electrode 17, depending on whether the device comprises a monopolar or bipolar electrode arrangement. Pulsing of the balloon can be performed by providing the balloon inflation channel with a pulsation pump to provide rapid deflation/inflation of the balloon using fluid, which may be a liquid or gas. Where one or more of the electrodes of the device is deployed into the expanded configuration mechanically via one or more wires incorporated within the device, the wires can be moved rapidly so as to pulse/move the electrode. Movement of the balloon or wires results in an oscillation of the surface between the internal vessel wall and the electrode, which helps to reduce tissue stick.

Another way of reducing sticking/adherence of one or more of the electrodes of the device to the vessel wall is to use a balloon comprising micropores in the balloon wall. These micropores allow for the release of fluid from the balloon, thereby reducing tissue stick and optionally also improving tissue recovery after the remodelling treatment. Substances, including drugs, may be administered to the site of treatment through the micropores in the balloon wall to improve tissue recovery.

In another embodiment of the invention, a further way or reducing or avoiding tissue stick/adherence is to continually or intermittently rotate and/or advance the device back and forth slightly (for example by a few millimeters) in the vessel during treatment. Rotation and/or lateral movement of the device may be controlled externally of the patient at the proximal end of the device by the user either manually or automatically using a rotation/lateral movement device. Continual or intermittent movement of the device helps to reduce the likelihood of the electrodes adhering to the vessel wall tissue.

In a specific embodiment of the invention shown in FIGS. 13(a) and (b) the washer 181 underlying the electrode 14 is deformable such that when the balloon 18 is fully inflated the washer 181 is displaced outwardly and occupies the spaces between the arms of the electrodes. In this way the surface of the washer 181 extends beyond that of the electrode 14 and in so doing bears upon and frees any tissue or occlusive material that has adhered to the surface of the electrode. In embodiments of the invention where the arms of the electrode 14 comprise one or more apertures the washer 181 may be deformed through the aperture 144 (see FIG. 13(b)) when the balloon is fully inflated.

In alternative embodiments of the invention (not shown), microwave energy, ultrasound energy, irreversible electroporation and an electric current are used (as heating elements) to apply thermal energy to remodel the internal surface topography of the hollow vessel.

In the case of microwave energy, two conducting cylinders can be mounted on the elongate body of the device 10 with a small interval between them such that they form a dipole antenna. The cylinders are connected to a coaxial cable which can be supplied with microwave energy at frequencies between 1 GHz and 5 GHz, suitably around 2-3 GHz. When microwave energy is applied to the coaxial cable the dipole will act as a source of microwave radiation, which will propagate as a cylindrical wave, depositing heat in the region next to the device 10. In a specific embodiment of the invention in use, the microwave energy used in remodelling is between 3 Watts and 100 Watts at a frequency of 2.45 Ghz. Suitable microwave dipole antennae are available from Microsulis™ (Hampshire, UK).

In the case of ultrasound energy, a cylinder of a piezoelectric material such as PZT-4 can be mounted on the distal end of the device 10. Electrodes, suitably made from silver, gold, or a titanium or tungsten alloy, are typically plated on the inner and outer surface of the cylinder. RF energy can be applied between the electrodes at an ultrasound frequency, for example the energy will typically be between 200 kHz and 20 MHz. This generates a cylindrical ultrasound wave which will radiate outwards and help to soften and mould the occluding mass.

In the case of electric current energy, aside from radiofrequency ablation, the electric current can take the form of resistive heating.

One way of monitoring the progress of the therapy phase is to include at least one temperature sensor (not shown), such as a thermocouple, in the devices of the invention. In embodiments of the invention where the device comprises a monopolar electrode arrangement, the temperature sensor may be located on the inert distal tip portion 12 or proximally to the electrode 14. In the embodiments of the invention where the catheter comprises a bipolar electrode arrangement the temperature sensor may be conveniently located between the electrodes 15 and 17. Clearly it is desirable that the therapy administered is sufficient to soften the occluding material 20. However, it may not be desirable to cause widespread and uncontrolled heating of potentially healthy tissue that is adjacent to the therapy site, of blood flowing along the vessel, or to induce closure of the hollow vessel, hence the option for improved control of the heating step.

In a further embodiment of the invention, the device 10 includes the capacity to induce a controlled level of tissue ablation if clinically necessary. For example, where a vessel is occluded by tumour tissue (see FIG. 1(b)) low power remodelling may be insufficient to ensure complete removal of the occlusion. Localised tissue ablation may be permitted by increasing the power output from the electrode (or other energy delivery means) to a level above that suitable for remodelling.

An alternative way of monitoring the progress of the therapy phase is to measure the level of electrical impedance. For instance, electrical impedance can be monitored during thermal remodelling and when a predefined threshold is reached the thermal remodelling phase is deemed to have been completed. It will be appreciated that the threshold will vary depending upon the type of occluding material.

A further method for monitoring the progress of the therapy phase is to include at least one flow sensor (not shown) in the devices of the invention. In embodiments of the invention where the device comprises a monopolar electrode arrangement, the flow sensor may be located proximally to the electrode 14 so as to measure the flow after the lumen of the vessel has been expanded by the monopolar electrode 14. In the embodiments of the invention where the catheter comprises a bipolar electrode arrangement the flow sensor may be conveniently located between the electrodes 15 and 17 and/or proximally to the proximal electrode 17. Once the flow has reached a predetermined level whereby the flow of blood through the vessel is deemed sufficient to supply organs and tissue, the therapy phase is complete.

Alternatively, a system is provided whereby the device is used in conjunction with a Doppler ultrasound flow sensor located externally to the patient.

In an embodiment of the invention, to image and position the device at the site of treatment, an external ultrasound transducer is used. The external ultrasound transducer is moved across the appropriate area of body of the patient in order to visualise the site of treatment. Ultrasound waves are emitted from the external transducer and penetrate through the body tissue towards the site of treatment. Incident ultrasound waves are reflected from the surface of the device and are detected by the external ultrasound transducer. One or more areas of increased ultrasound reflection (echogenic surfaces) can be provided on the surface of the device and/or the surface of the guidewire, if used, to increase the ultrasound reflection and improve visualisation of the device at the site of treatment.

A piezoelectric material such as PZT (lead zirconate titanate) or PVDF (polyvinylidene fluoride) can be mounted adjacent to the monopolar electrode of the device, or adjacent to and/or between the bipolar electrodes of the device, as appropriate, and excited with an external ultrasound signal. Single or multiple PZT or PVDF elements can be used and the elements can take the form of a ring, crystal or film of piezoelectric material. The signal generated by the PZT or PVDF elements is detectable by the external ultrasound transducer.

In another embodiment of invention, the device is provided with an ultrasound transmitter at its distal end to assist with navigation. The ultrasound signal may be received by an external ultrasound receiver/sensor located on the surface of the body of the patient. Ultrasound waves emitted from the internal ultrasound transmitter are reflected off the surface of the device and are detected by the external ultrasound transducer.

In another embodiment of the invention (not shown), a microwave or electromagnetic transmitter is located at the distal end of the device and is used to assist with navigation of the device under ultrasound scan, CT or MRI. The transmitter may be an electromagnetic coil that can be received by a set of external reference coils, such as the Flock of Birds system (Ascension Technologies, Burlington, Vt.) to give a 3D position. Alternatively, the electromagnetic transmitter may be an MR tracking coil.

To enhance visualisation of the device 10 under MRI, gadolinium, indium and/or tantalum can be incorporated into the device, for example in the form of a coiled wire on the surface of the device or embedded in a polymer in the form of a paint.

In an embodiment of the invention, the device can be configured so as to emit local radiotherapy, i.e. brachytherapy or internal radiotherapy, at the site of treatment. This is useful in instances where vessel obstruction is due to a cancerous tumour in or around the vessel. By performing local radiotherapy, rather than external beam radiotherapy, the exposure of healthy tissue to radiation is reduced. Local radiotherapy may be emitted from the device by providing a microwave or RF radiation source at the tip of the device, or at any another suitable location on the device such as proximally to the distal electrode. Alternatively, an iridium-192 impregnated wire may be placed at the tip of the catheter or may be located in the guidewire lumen of the catheter and exposed at the tip of the catheter so as to emit local radiotherapy.

In all embodiments of the invention, the catheter body is suitably manufactured from plastics or polymeric biocompatible materials known in the technical field, for example, PTFE. In one embodiment of the invention (not shown), the device catheter body may be manufactured from a flexible material so as to enable the device to follow the natural curvature of the lumen of the vessel through which it is travelling.

The electrodes of the invention are suitably constructed from a biocompatible metal such as stainless steel, platinum, silver, titanium, gold, a suitable alloy, gold plated beryllium copper and/or a shape memory alloy such as Nitinol. The distance between the bipolar electrodes will, to an extent, define the shape of the thermal energy pattern and the extent of the penetration of energy into the occluding structure. Greater separation between the electrodes tends to result in two distinct foci or regions of thermal energy, whereas closer spacing allows the areas of thermal energy to converge into a single elongated region. According to the invention, the distal and proximal bipolar electrodes are typically spaced no more than approximately 15 mm apart, and suitably between around 7 mm and about 10 mm or 12 mm apart.

The catheters of the invention are suitably constructed in a variety of sizes typically ranging from 0.6 mm up to 2.6 mm in diameter (corresponds to French sizes 2 to 8). Guidewires for use with catheters of the invention are typically in the size range of 0.05 mm to about 1 mm (about 0.002 inches to about 0.05 inches). Thus, the catheters of the invention can be used by the clinician to remodel the lumens of a wide range of blood vessels from large arteries to smaller arterioles and veins, and to administer therapy in locations previously considered to be inaccessible to surgery.

The devices of the invention can also be used during endoscopic and laparoscopic procedures where the vessel includes the bile duct, the intestine, the fallopian tubes, the ureter, the urethra, the esophagus, bronchioles, or any other hollow vessel within the body of an animal. The device of the invention may be used in combination with a guidewire in monorail or over-the-wire configurations, or without a guidewire in combination with a guide catheter or passed along a lumen of an endoscope.

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the spirit and scope of the invention as defined by the claims. In addition, the above described embodiments may be used in combination unless otherwise indicated.

The invention claimed is:

1. A device suitable for remodeling the internal surface of a hollow vessel which vessel is at least partially occluded by a mass, the device comprising: an elongate body having a distal end and a proximal end, the distal end comprising a tip portion located at the distal terminus of the body, a bipolar radiofrequency electrode arrangement located proximally to the tip portion within the distal end, and at least one expandable bladder located within the distal end tip portion;

wherein the bipolar radiofrequency electrode arrangement comprises a first electrode located proximally to the tip portion within the distal end of the elongate body and a second electrode located at a position proximally to the first electrode;

wherein the first electrode is located at least partially over the at least one bladder and wherein the first electrode is cone shaped and configured so as to be greater in dimension proximally than distally and thereby tapers towards the distal end of the elongate body when in both an unexpanded and an expanded configuration;

wherein the first electrode is arranged so that it can be deployed outwardly from the body of the device and in so doing exert an expansion force on the hollow vessel; and, wherein the bipolar radiofrequency electrode arrangement is capable of delivering energy up to about 50 Watts so as to remodel the internal surface of the hollow vessel without inducing closure of the hollow vessel.

2. The device according to claim 1, wherein the bipolar radiofrequency electrode arrangement is capable of delivering energy up to about 30 Watts.

3. The device according to claim 1, wherein the bipolar radiofrequency electrode arrangement delivers energy for a period of up to about 5 minutes.

4. The device according to claim 1, wherein the first electrode is located on a bladder which is capable of being inflated so as to expand the first electrode.

5. The device according to claim 1, wherein the first electrode is selected from the group consisting of: an expandable umbrella/cone structure; an expandable single helical coil; an expandable double helical coil; and an expandable basket structure.

6. The device according to claim 1, wherein the second electrode is arranged so that it can be deployed outwardly from the body of the device and in so doing exert an expansion force on the hollow vessel.

7. The device according to claim 6, wherein the second electrode is located on a bladder which is capable of being inflated so as to expand the second electrode.

8. The device according to claim 6, wherein the second electrode comprises an expandable basket structure.

9. The device according to claim 6, wherein the second electrode comprises an expandable umbrella/cone structure and is configured so as to be greater in dimension distally than proximally and thereby tapers towards its proximal end.

10. The device according to claim 1, wherein the elongate body comprises a channel extending along at least a portion of the length of the elongate body for the aspiration of dislodged occluding matter from the lumen of the hollow vessel.

11. The device according to claim 1, wherein the elongate body further comprises a filter located towards the proximal end of the elongate body for the collection of any occluding matter which has been dislodged from the lumen of the hollow vessel.

12. The device according to claim 11, wherein the filter comprises an expandable umbrella structure.

13. The device according to claim 1, wherein the elongate body comprises a guidewire channel extending along at least a portion of the length of the elongate body, wherein the guidewire channel is configured to enable slidable mounting of the device upon a guidewire.

14. The device according to claim 1, wherein the device is provided with a microwave or RF or iridium-192 radiation source at its distal end for performing local radiotherapy at the site of treatment.

15. The device according to claim 1, wherein the hollow vessel is a blood vessel and wherein the mass comprises an atheromatous plaque, a tumor or a thrombosis.

16. A method for remodeling the internal surface of a hollow vessel at a predetermined site within the body of a patient comprising:
a) introducing a device according to claim 1 into the hollow vessel;
b) directing the device towards the predetermined site within the body of the patient;
c) delivering energy up to about 50 Watts to the hollow vessel so as to remodel the internal surface of the hollow vessel without inducing closure of the hollow vessel;
d) monitoring the delivery in step (c);
e) ceasing energy delivery when the internal surface of the hollow vessel has been sufficiently remodeled;
f) withdrawing the device from the hollow vessel.

17. The method according to claim 16, wherein step c) comprises delivering energy up to about 30 Watts.

18. The method according to claim 16, wherein step c) further comprises
expanding the first electrode to exert an expansion force on the hollow vessel.

19. The method according to claim 18, wherein step c) further comprises pulsing the first electrode between its unexpanded and expanded configuration so as to avoid adherence of the device to the wall of the hollow vessel during treatment.

20. The method according to claim 16, wherein step c) further comprises continuously rotating the device and/or advancing the device back and forth in the hollow vessel so as to avoid adherence of the device to the wall of the hollow vessel during treatment.

* * * * *